(12) United States Patent
Weiner et al.

(10) Patent No.: US 7,875,632 B2
(45) Date of Patent: *Jan. 25, 2011

(54) SELECTIVE SEROTONIN RECEPTOR INVERSE AGONISTS AS THERAPEUTICS FOR DISEASE

(75) Inventors: David M. Weiner, San Diego, CA (US); Robert E. Davis, San Diego, CA (US); Mark R. Brann, Del Mar, CA (US)

(73) Assignee: ACADIA Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/378,385

(22) Filed: Feb. 11, 2009

(65) Prior Publication Data

US 2009/0155389 A1 Jun. 18, 2009

Related U.S. Application Data

(63) Continuation of application No. 10/854,035, filed on May 24, 2004, now abandoned, which is a continuation-in-part of application No. 10/850,819, filed on May 21, 2004.

(51) Int. Cl.
*A61K 31/445* (2006.01)
*A61P 25/00* (2006.01)

(52) U.S. Cl. .................... 514/317; 514/225.5; 514/277; 514/469; 514/588; 514/595

(58) Field of Classification Search .................. 514/217, 514/317, 469, 722, 378, 618, 225, 277, 225.5, 514/588, 595

See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,401,665 A | 8/1983 | Sheinaus et al. |
| 4,853,394 A | 8/1989 | King et al. |
| 4,908,369 A | 3/1990 | Schechter et al. |
| 5,025,013 A | 6/1991 | Barreau et al. |
| 5,214,044 A | 5/1993 | Cooper et al. |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue et al. |
| 5,869,488 A | 2/1999 | Shue et al. |
| 5,874,445 A | 2/1999 | Carr et al. |
| 5,877,173 A | 3/1999 | Olney et al. |
| 5,912,132 A | 6/1999 | Brann |
| 5,952,324 A | 9/1999 | Barbachyn et al. |
| 5,955,281 A | 9/1999 | Brann |
| 6,107,324 A | 8/2000 | Behan et al. |
| 6,140,509 A | 10/2000 | Behan et al. |
| 6,150,393 A | 11/2000 | Behan et al. |
| 6,358,698 B1 | 3/2002 | Weiner et al. |
| 6,479,480 B1 | 11/2002 | Moyes et al. |
| 6,486,153 B1 | 11/2002 | Pineiro et al. |
| 6,617,339 B1 | 9/2003 | Gravestock |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,115,634 B2 | 10/2006 | Thurieau et al. |
| 7,253,186 B2 | 8/2007 | Andersson et al. |
| 7,601,740 B2 | 10/2009 | Weiner et al. |
| 2002/0004513 A1 | 1/2002 | Andersson et al. |
| 2002/0035145 A1 | 3/2002 | Tsai et al. |
| 2002/0156068 A1 | 10/2002 | Behan et al. |
| 2002/0165225 A1 | 11/2002 | Hamied et al. |
| 2003/0092700 A1 | 5/2003 | Czollner et al. |

(Continued)

FOREIGN PATENT DOCUMENTS

CA 984843 3/1976

(Continued)

OTHER PUBLICATIONS

Acadia Pharmaceuticals Announces Results from Phase III Trial of Pimavanserin in Parkinson's Disease Psychosis Acadia Pharmaceuticals Announces Results from Phase III Trial of Pimavanserin in Parkinson's Disease Psychosis, Press Release (Business Wire, San Diego), Sep. 1, 2009.

(Continued)

*Primary Examiner*—Sreeni Padmanabhan
*Assistant Examiner*—Sahar Javanmard
(74) *Attorney, Agent, or Firm*—Jones Day

(57) ABSTRACT

Disclosed herein are pharmaceutical compositions comprising an inverse serotonin receptor agonist or a serotonin receptor antagonist and an anti-psychotic agent. Disclosed herein are also methods of treating psychotic disorders using the disclosed pharmaceutical compositions.

11 Claims, No Drawings

U.S. PATENT DOCUMENTS

| | | | |
|---|---|---|---|
| 2003/0220316 | A1 | 11/2003 | Andersson et al. |
| 2004/0006081 | A1 | 1/2004 | Burrows et al. |
| 2004/0106600 | A1 | 6/2004 | Andersson et al. |
| 2004/0213816 | A1 | 10/2004 | Weiner et al. |
| 2005/0014757 | A1 | 1/2005 | Andersson et al. |
| 2005/0148018 | A1 | 7/2005 | Weiner et al. |
| 2005/0244862 | A1 | 11/2005 | Brann |
| 2005/0256108 | A1 | 11/2005 | Schlienger |
| 2006/0094758 | A1 | 5/2006 | Andersson et al. |
| 2006/0106063 | A1 | 5/2006 | Thygesen et al. |
| 2006/0111399 | A1 | 5/2006 | Thygesen et al. |
| 2006/0194778 | A1 | 8/2006 | Andersson et al. |
| 2006/0194834 | A1 | 8/2006 | Andersson et al. |
| 2006/0199794 | A1 | 9/2006 | Schlienger |
| 2006/0199818 | A1 | 9/2006 | Andersson et al. |
| 2006/0199842 | A1 | 9/2006 | Weiner et al. |
| 2006/0205710 | A1 | 9/2006 | Schlienger et al. |
| 2006/0205722 | A1 | 9/2006 | Andersson et al. |
| 2006/0205780 | A1 | 9/2006 | Thygesen et al. |
| 2006/0205781 | A1 | 9/2006 | Thygesen et al. |
| 2006/0264465 | A1 | 11/2006 | Weiner et al. |
| 2006/0264466 | A1 | 11/2006 | Weiner et al. |
| 2006/0286610 | A1 | 12/2006 | Brann |
| 2006/0292606 | A1 | 12/2006 | Brann |

FOREIGN PATENT DOCUMENTS

| | | |
|---|---|---|
| EP | 0 005 318 | 11/1979 |
| EP | 0 056 144 | 7/1982 |
| EP | 0 061 333 | 9/1982 |
| EP | 0 379 441 | 7/1990 |
| EP | 0 548 015 | 6/1993 |
| EP | 0 260 070 | 8/1993 |
| EP | 0 625 507 | 11/1994 |
| EP | 1 656 938 | 5/2006 |
| FR | 2802206 | 6/2001 |
| HU | 157325 | 3/1998 |
| JP | 51052176 | 5/1976 |
| JP | 5208517 A | 5/1977 |
| WO | WO 94/27967 | 12/1994 |
| WO | WO 97/08166 | 3/1997 |
| WO | WO 97/11940 | 4/1997 |
| WO | WO 97/38665 | 10/1997 |
| WO | WO 97/38984 | 10/1997 |
| WO | WO 98/11128 | 3/1998 |
| WO | WO 98/17646 | 4/1998 |
| WO | WO 98/44921 | 10/1998 |
| WO | WO 98/50534 | 11/1998 |
| WO | WO 99/52927 | 10/1999 |
| WO | WO 00/23076 | 4/2000 |
| WO | WO 00/56335 | 9/2000 |
| WO | WO 00/59497 | 10/2000 |
| WO | WO 00/69810 | 11/2000 |
| WO | WO 01/44191 | 6/2001 |
| WO | WO 01/66521 | 9/2001 |
| WO | WO 01/87839 | 11/2001 |
| WO | WO 02/24649 | 3/2002 |
| WO | WO 02/076464 | 10/2002 |
| WO | WO 02/079186 | 10/2002 |
| WO | WO 03/057698 | 7/2003 |
| WO | WO 03/062206 | 7/2003 |
| WO | WO 03/070246 | 8/2003 |
| WO | WO 03/086400 | 10/2003 |
| WO | WO 2004/000808 | 12/2003 |
| WO | WO 2004/009549 | 1/2004 |
| WO | WO 2004/064738 | 8/2004 |
| WO | WO 2004/072034 | 8/2004 |
| WO | WO 2005/042502 | 5/2005 |
| WO | WO 2005/053796 | 6/2005 |
| WO | WO 2005/063254 | 7/2005 |
| WO | WO 2005/112927 | 12/2005 |
| WO | WO 2005/115361 | 12/2005 |
| WO | WO 2006/036874 | 4/2006 |
| WO | WO 2006/037043 | 4/2006 |
| WO | WO 2006/104826 | 10/2006 |
| WO | WO 2004/039322 | 5/2007 |

OTHER PUBLICATIONS

Acadia Pharmaceuticals Provide Update on Pimavanserin Collaborative Development Program, Press Release (Business Wire, San Diego), Oct. 6, 2009.

Adam, et al. "Effects of repeated ritanserin on middle-aged poor sleepers," Psychopharmacology, 99:219-221 (1989).

Adell, et al., "Strategies for producing faster acting antidepressants," Drug Discovery Today, 10(8):578-585 (2005).

Akin, et al., "Decreased serotonin 5-HT2A receptor-stimulated phosphoinositide signaling in fibroblasts from melancholic depressed patients," Neuropsychopharmacology, 29:2081-2087 (2004).

Alvisi, "Sulla formazione di derivati pirazolici dalle didoridrine e dalla tribromidrina della glicerina ordinaria," Gazz. Chem. Ital. 22:158-168 (1892).

Antilla, at al., "Copper-catalyzed coupling of arylboronic acids and amines," Organic Letters, 3(13):20n-2079 (2001).

Antilla, et al., "The copper-catalyzed N-arylation of indoles," J. Am. Chem. Soc., 124:11684-11688 (2002).

Archibald et al., "Benzamidopiperdines. 3. Heterocydic Compounds Related to Indoramin," J. Medicinal Chemistry, 17(7):-739-744 (1974).

Archibald et al., "1,4-Bis-(2-indol-3-ylethyl)piperdines," J. Medicinal Chemistry, 17(7):-745-747 (1974).

Archibald, et al., "Benzamidopiperdines. 2. Heterocydic Compounds Related to Indoramin," J. Medicinal Chemistry, 17(7):736-739 (1974).

Artico et al., "Aromatic hydrazides as specific inhibitors of bovine serum amine oxidase," Eur. J. Med. Chem., 27:219-228 (1992).

Avemaria et al., "Sythesis of aryl azides via post-cleavage modifications of polymer-bound triazenes," Synlett 7:1163-1166 (2004).

Bakshi et al., "Clozapine antagonizes phencydidine-induced deficits in sensorimotor gating of the startle response," The Journal of Pharmacology and Experimental Therapeutics, 271(2):787-794 (1994).

Barchas et al., Serotonin and behavior, pp. 483-498, 523-560 (1973), NY: Academic Press.

Barnes et al., "A review of central 5-HT receptors and their function," Neuropharmacology, 38: 1083-1152 (1999).

Barr et al., "Agonist-independent activation of Gz by the 5-hydroxytryptamine$_{1A}$ receptor co-expressed in Spodootera frugiperda cells," The Journal of Biological Chemistry, 272(52):32979-32987 (1997).

Bassus et al., "Psychotropes potentiels. X. Synthese de butyrophenones a cycle piperidine-spiro-tetrahydrooxazinone douees d'activite neuroleptique," Eur. J. Med. Chem. -Chimica Therapeutica, 9(4):416-423 (1974).

Benfield et al., "Fluoxetine. A review of its pharmacodynamic & pharmacokinetic properties, & therapeutic efficacy in depressive illness," Drugs, 32(6):491-508 (1986).

Benfield et al., "Fluoxetine, A review of its pharmacodynamic and pharmacokinetic properties, and therapeutic efficacy in depressive illness", Drugs, 32(6), pp. 481-508 (1986).

Benke, at al., Chemical Abstracts, 73:25305. (1970).

Bennett et al., Suppression of dyskinesias in advanced Parkinson's disease. II. Increasing daily clozapine doses suppress dyskinesias and improve parkinsonism symptoms, Neurology, 43:1551-1555 (1993).

Bhatia et al., "5-Lipoxygenase inhibitors: Synthesis and structure-activity relationships of a series of 1-Arvl-2H,4H-tetrahvdro-1,2,4-triazin-3-ones," J. Med. Chem., 39:3938-3950 (1996).

Biagi et al., "1,2,3-Triazoles: Structural changes on two effective inhibitors of the prostaglandin synthesis in vitro," Farmaco Ed. Sci., 43:597-612 (1988).

Bibbiani et al., "Serotonin 5-HT1A agonist improves motor complications in rodent and primate parkinsonian models," Neurology, 57:1829-1834 (2001).

Birkmayer et al., "Nucleus ruber and L-Dopa psychosis: Biochemical post-mortem findings," Journal of Neural Transmission, 35:93-116 (1974).

Blakley, et al., "Bidirectional changes in ethanol consumption in rats with site-specific antisense down-regulation of 5-hydroxytryptamine$_{2A}$ receptors in brain," The Journal of Pharmacology and Experimental Therapeutics, 299(1):277-289 (2001).

Blier et al., "Potential mechanisms of action of atypical antipsychotic medications in treatment-resistant depression and anxiety," J. Clin. Psychiatry, 66(suppl 8):30-40 (2005).

Blier et al., "Putative mechanisms of action of antidepressant drugs in affective and anxiety disorders and pain," Journal of Psychiatry & Neuroscience, 26(1):37-43 (2001).

Bond et al., "Physiological effects of inverse agonists in transgenic mice with myocardial overexpression of the $\beta_2$-adrenoceptor," Nature, 374:272-276 (1995).

Borman et al., "5-HT2B receptors play a key role in mediating the excitatory effects of 5-HT in human colon in vitro", Br. J. Pharmacol., 135(5): 1144-1151 (2002).

Bouillin, "Serotonin in mental abnormalities", pp. 119-181 (1978).

Boullin, Serotonin in Mental Abnormalities (p. 316). New York: Wiley (1978).

Brann, "Identification of ligands by selective amplification of celles transfected with receptors and marker enzymes", Chem. Abstr. 128:111548 (1998) and citations therein.

Brown et al, "Catalytic alkylation of aniline," J. Am. Chem. Soc., 46(8):1836-1839 (1924).

Buchi et al., "Synthesis of (±)-nuciferal," J. Org. Chem., 34(4):1122-1123 (1969).

Butcher et al., L-Dopa induced changes in central monoamine neurons after peripheral decarboxylase inhibition: Letters to the Editor, J. Pharm. Pharmac., 22:313-316 (1970).

Buu-Ho et al., Further studies in the alkylation of phenols and thiophenels: J. Org. Chern., 16:988994 (1951).

Cacchi et al., "Palladium-catalyzed reaction of aryl iodides with acetic anhydride. A carbon monoxide-free synthesis of acetophenones," Organic Letters, 5(3):289-291 (2003).

Carman, et al. 1998. A further synthesis of an analogue of the antifungal/antiherbivore lipid from avocado. *Aust. J. Chem.*, 51:955-959.

Caroon et al., "Synthesis and antihypertensive activity of a series of 8-substituted 1-Oxa-3,8diazaspiro[4.5]decan-2-ones," J. Med. Chem., 24:1320-1328 (1981).

Carroll et al., Synthesis and muscarinic receptor activity of ester derivatives of 2-substituted 2azabicyclof2.2.llheotan-5-ol and -6-01,• J. Med. Chem. 35:2184-2191 (1992).

Catarzi et al., "Synthesis, ionotropic glutamate receptor binding affinity, and structure-activity relationships of a new set of 4,5-dihydro-8-heteroaryl-4-oxo-1,2,4-triazolo[1,5-a]guinoxaline-2-carboxylates analogues of TQX-173," J. Med Chem., 44:3157-3165 (2001).

Cerione et al., "The mammalian $\beta_2$-adrenergic receptor: Reconstitution of functional interactions between pure receptor and pure stimulatory nucelotide binding protein of the adenylate cyclase system," Biochemistry, 23:4519-4525 (1984).

Cherkasov et al., "Organothiophosphorus reagents in organic synthesis," Tetrahedron, 41(13):2567-2624 (1985).

Choi et al., 5-HT2B recepto-mediated serotonin morphogenic functions in mouse cranial neural crest and myocardiac cells, Development, vol. 124, pp. 1745-1755 (1997).

Clark et al., "Antihypertensive 9-substituted 1-Oxa-4,9-diazaspiro[5.5]undecan-3-ones," J. Med. Chem., 26:855-861 (1983).

Clifton et al., "Arylethanolamines derived from salicyclamide with α- and β-adrenoceptor blocking activities. Preparation of Labetalol, its enantiomers, and related salicyclamides," J. Med. Chem., 25:670679 (1982).

Cox, Medicinal Chemistry -28th International Symposium: Jun. 8-12, 2002, San Diego, CA, USA, Drugs, 5(7):626-632 (2002).

DeClerck, et al., "Increase in slow-wave sleep in humans with the serotonin-S$_2$ antagonist ritanserin," Current Therapeutic Research, 41 (4):427-432 (1987).

Delecluse et al., "A case of tardive tremor successfully treated with clozapine," Movement Disorders, 13(5):846-847 (1998).

Dorwald, "Side reactions in organic synthesis: A guide to successful synthesis design", Wiley-VCH GmbH & KGaA, Wienheim (2005).

Dunn et al., "Analgetic and antiinflammatory 7-aroylbenzofuran-5-ylacetic acids and 7-arovlbenzothiophene-5-ylacetic acids," J. Med. Chem., 29:2326-2329 (1986).

Durif et al., "Low-dose clozapine improves dyskinesias in Parkinson's disease," Neurology, 48:658662 (1997).

Eichelbaum et al., "Influence of pharmacogenetics on drug disposition and response," Clinical and Experimental Pharmacology and Physiology, 23:983-985 (1996).

Emerson, et al., "The reductive alkylation of aniline," J. Am. Chem. Soc., 60:2023-2025 (1938).

Ermakov et al., "Use of Mass spectrometry in structural and stereochemical studies," Chemistry of Heterocyclic Compounds, 1:72-77 (1981).

Everett et al., "L-Dopa: Effect on concentrations of dopamine, norepinephrine, and serotonin in brains of mice," Science, 168:849-850 (1970).

Factor, S.A., et al. "Clozapine for the Treatment of Drug-Induced Psychosis in Parkinson's Disease: Results of the 12 Week Open Label Extension in the PSYCLOPS Trial." (Movement Disorders Official Journal of the Movement Disorder Society), Jan. 2001, vol. 16, No. 1: 135-139.

Factor, S.A., et al. "Clozapine Prevents Recurrence of Psychosis in Parkinson's Disease." (Movement Disorders Official Journal of the Movement Disorder Society), 1992, vol. 7, No. 2: 125-131.

Finar et al., The preparation and properties of some derivatives of 1-phenylpyrazole: J. Chem. Soc., pp. 2293-2298 (1954).

Fisera et al., Synthesis of spiro-substituted 1,3-oxazines by a new sequence leading to spiroheterocvcles: Monatshefte fur Chemie, 125:909-919 (1994).

Fitzgerald et al., "Possible role of vavular serotonin 5-HT2B receptors in the cardiopathy associated with fenfluramine", Molecular Pharmacol., vol. 57, pp. 75-81 (1999).

French Clozapine Study Group (THE), "Clozapine in drug-induced psychosis in Parkinson's disease", Lancet, 353:2041-2042 (1999).

Friedman et al., "Atypical antipsychoties in the treatment of drug-induced psychosis in Parkinson's disease," Movement Disorders, 15(2):201-211 (2000).

Friedman et al., Low-dose clozapine for the treatment of drug-induced psychosis in Parkinson's disease: N. Engl. J. Med., 340(10):757-763 (1999).

Friedman, J.H., "Clozapine Treatment of Psychosis in Patients with Tardive Dystonia: Report of Three Cases." (Movement Disorders Official Journal of the Movement Disorder Society), May 1994, vol. 9, No. 3:321-324.

Fuller, Drugs acting on serotonergic neuronal systems. In N. N. Osborne (Ed.), Biology of Serotoneroic Transmission, Chap. 9, pp. 221-247. New York: Wiley (1982).

Gainetdinov et al., "Genetic animal models: Focus on schizophrenia," Trends in Neurosciences, 24(9)527-533 (2001).

Gamma et al., 3,4-Methylenedioxymethamphetamine (MDMA) modulates cortical and limbic brain activity as measured bv 1li21501-PET in healthy humans: NeuroosvchoDhannacoloov, 23(4):388-395 (2000).

Gawley et al., Principles of Asymmetric Synthesis. New York: Pergamon (1996).

Gershon, "5-Hydroxytryptamine and enteric neurones." In J. R. Fozard (Ed.), The Peripheral Actions of 5-Hydroxyfryptamine (pp. 247-273), New York: Oxford University Press (1989).

Gillman, "Monoamine oxidase inhibitors, opioid analgesics and serotonin toxicity," British Journal of Anaesthesia, 95(4):434-441 (2005).

Glazer, W.M., "Extrapyramidal side effects, tardive dyskinesia, and the concept of atypicality", J. Clin. Psychiatry, vol. 61, Supp. 3, pp. 16-21 (2000).

Glennon, "Serotonin receptors: Clinical implications," Neuroscience & Biobehavioral Reviews, 14:35-47 (1990).

Gooben et al., "Palladium-catalyzed synthesis of aryl ketones from boronic acids and carboxylic acids or anhydrides," Angew. Chem. Int. Ed., 40:3458-3460 (2001).

Goodman and Gilman's The pharmacological basis of therapeutics, 7th edition, pp. 340-343 and 403-404.

Goodman et al., The Pharmacological Basis of Therapeutics, McGraw Hill, 9th ed., pp. 434-435 (1996).

Gstach et al., "Rearrangement of 3,3-disubstituted 1-aryl-4,5-dihydro-5-oxo-3H-1,2,4-triazolium tetraflluoroborates; Part 1. A versatile synthesis of 1,5-disubstituted 2-aryl-1,2-dihydro-3H-1,2,4-triazol-3one tetrafluoroborates," Synthesis, pp. 803-808 (1990).

Guthrie, et al. 1993. The tetrahedral intermediate from the hydration of N-methylformanilide. Can. J. Chem., 71:2109-2122.

Harper et al., "The chemistry and pharmacology of some 4-aminopiperidines and their derivatives," J. Med. Chem., 44:729-732 (1964).

Hartwig, "Transition metal catalyzed synthesis of arylamines and aryl ethers from aryl halides and triflates: Scope and mechanism," Angew. Chem. Int. Ed., 37:2047-2067 (1998).

Herrick-Davis, et al. "Inverse Agonist Activity of Atypical Antipsychotic Drugs at Human 5-Hydroxytryptamine2C Receptors" (The Journal of Pharmacology and Experimental Therapeutics), Oct. 2000, vol. 295, No. 1: 226-232.

Hickinbottom, "The preparation of secondary alkylaryl-amines and their purification," J. Chem. Soc., pp. 992-994 (1930).

Hirst et al., "A method for preparing the formyl derivatives of the aromatic amines," J. Chem. Soc., 67:829-831 (1895).

Idzikowski et al., "A dose response study examining the effects of manserin on human slow wave sleep," Br. J. Clin. Pharmac., 31:193-196 (1991).

Irikura et al. 1971 "New Anticulcer Agents. 1. Synthesis and Biological Activities of 1-Acyl-2-,-3-,-4- substituted Benzamidopiperdines" J. Medical Chemistry 14(4): 357-361.

Ito et al., "Prediction of human drugs clearance from in vitro and preclinical data using physiologically based and emperical approaches", Pharm. Res., 22(1), pp. 103-112 (2005).

Jaeger, et al. 1941. Tow ketones of the stilboestrol group. J. Chem. Soc., 744-747.

Johnston et al., "Drugs in Development for Parkinson's Disease: An Update," Current Opin. Investig. Drugs, vol. 7, No. 1, pp. 25-32 (2006).

Julius et al., "The 5H2T receptor defines a family of structurally distinct but functionally conserved serotonin receptors," Proc. Nato. Acad. Sci. USA 87:928-932.

Kalgutkar, et al. 1995. Selective inhibitors of monoamine oxidase (MAO-A and MAO-B) as probes of its catalytic site and mechanism. Medicinal Research Reviews, 15(4)325-388. XP002034298.

Kanayama, et al. 2005. New treatment of lumbar disc herniation involving 5-hydroxytryptamine2A receptor inhibitor: A randomized controlled trial. J. Neurosurg: Spine, 2:441-446.

Kay, G.G., "The effects of antihistamines in cognition and performance", J. Allergy Clin. Immunol., 105(6), Pt. 2, pp. S622-S627 (2000).

Klapars, et al. 2001. A general and efficient copper catalyst for the amidation of aryl halides and the N-arylation of nitrogen heterocycles. J. Am. Chem. Soc. 123:7727-7729.

Klapars, et al. 2002. A general and efficient copper catalyst for the amidation of aryl halides. J. Am. Chem. Soc., 124:7421-7428.

Kuehne, et al. 1991(a). Enantioselective syntheses of vinblastine, leurosidine, vincovaline, and 20'-epi-vincovaline. J. Org. Chem., 56(2):513-528.

Kuehne, et al. 1991(b). Total syntheses of Yohimbe alkaloids, with stereoselection for the normal, allo, and 3-epiallo series, based on annelations of 4-methoxy-1, 2-dihydropyridoes. J. Org. Chem. 56(8):2701-2712.

Kwong, et al. 2002(a). Copper-catalyzed coupling of alkylamines and aryl iodides: An efficient system even in an air atmosphere. Organic Letters 4(4):581-584.

Kwong, et al. 2002(b). A general, efficient, and inexpensive catalyst system for the coupling of aryl iodides and thiols. Organic Letters, 4(20):3517-3520.

Kwong, et al. 2003. Mild and efficient copper-catalyzed amination of aryl bromides and primary alkylamines. Organic Letters, 5(6)793:796.

Landini, et al. 1974. A convenient synthesis of primary and secondary dialkyl and aryl alkyl sulfides in the presence of phase-transfer catalysts. Synthesis, p. 565-566.

Landolt, et al. 1999. Serotonin-2 receptors and human sleep: Effect of a selective antagonist on EEG power spectra. Neuropsychophamacology, 21(3) 455-466.

Letter in response to Written Opinion of the Preliminary Examining Authority in PCT/US2004/001234, dated Mar. 14, 2005.

Leysen, J., E., Niemegeers, C., J., Tollenaraere, J., P., and Laduron, P., M. (1978) "Serotonergic component of neuroleptic receptors," Nature (Lond) 272: 168-171.

Li, G. Y. 2002. Highly active, air-stable palladium catalysts for the C-C and C-S bond-forming reactions of vinyl and aryl cholrides: Use of commercially available [(t-Bu)2P(OH)]2PdCl2, [(t-Bu)2P(OH)PdCl2]2 and [(t-Bu)2PO . . . H . . . OP(t-Bu)2PdCl]2 as catalysts. J. Org. Chem., 67:3643-3650.

Liechti, M., E., Geyer, M., A., Hell, D., and Vollenwieder, F., X. (2001) "Effects of MDMA(ecstasy) on Prepulse Inhibition and Habituation on Startle in Humans after Pretreatment with Citalopram, Haloperidol, or Ketanserin," Neuropsychopharmacology, 24(3): 240-252.

Linder, "Pharmacogenetics: a laboratory tool for optimizing therapeutic efficiency," Clin. Chem. 43:254-66 (1997).

Lowe, et al. 1994. Aza-tricyclic substance P antagonists. J. Med. Chem., 37:2831-2840.

Mansbach, et al. 1988. Dopaminergic stimulation disrupts sensorimotor gating in the rat. Psychopharmacology, 94:507-514.

March, et al., Journal of Advanced Organic Chemistry: Reactions, Mechanism and Structure, 5th Edition, p. 423.

Marek et al. 2003. Synergistic action of 5-HT2A antagonists and selective serotonin reuptake inhibitors in neuropsychiatric disorders. Neuropsychopharmacology, 28:402-412.

Marek et al. 2005. The selective 5-HT2A receptor antagonist M100907 enhances antidepressant-like behavioral effects of the SSRI fluoxetine. Neuropsychopharmacology, 30:2205-2215.

Marek et al., "Synergistic Action of 5-HT 2A Antagonists and Selective Serotonin Reuptake Inhibitors in Neuropsychiatric Disorders," Neuropsychopharmacology, 2003, 28: 402-412.

Maubach, K., "Psychiatric Drug Discovery and Development," Expert Opin. Investig. Drugs., vol. 12, No. 9, pp. 1571-1575 (2003).

Mavunkel, et al. 1996. Synthesis and characterization of pseudopeptide bradykinin B2 receptor antagonists containing the 1,3,8-triazaspiro[4.5]decan-4-one ring system. J. Med. Chem., 39:3169-3173.

Mayer, et al. 2003. Ritanserin improves sleep quality in narcolepsy. Pharmacopsychiatry, 364:150-155.

Meltzer, "The Role of Serotonin in Antipsychotic Drug Action," Neuropsychopharmacology, 21:I06S-I15S (1999).

Meltzer, et al., "Serotonin Receptors: Their Key Role in Drugs to Treat Schizophrenia," Progress in Neuro-Pyschopharmacology & Biol. Psych., vol. 27, pp. 1159-1172 (2003).

Meltzer, H., Y., Kennedy, J., Dai, J., Parsa, M., and Riley, D. (1995) "Plasma Clozapine Levels and the Treatment of L-DOPA-Induced Psychosis in Parkinson's Disease. A High Potency Effect of Clozapine," Neuropsychopharmacology, 12(1): 39-45.

Meng, et al. 1991. Synthetic approaches toward glidobamine, the core structure of the glidobactin antibiotics. Tetrahedron, 47(32):62510-6264.

Micovic, et al. 1991. A simple method for preparation of secondary aromatic amines. Synthesis, 11:1043-1045.

Miyata, et al. 2000. Sarpogrelate, a selective 5-HT2A serotonergic receptor antagonist, inhibits serotonin-induced coronary artery spasm in a porcine model. Journal of Cardiovascular Pharmacology, 35(2) 294-301.

Möhrle, et al. 1990. Sodium mercury edetate dehydrogenation of N-aliphatic substituted 1,2,3,6-tetrahydropyridine derivatives. Arch. Pharm. (Weinheim), 323:109-115.

Morgan et al., "Emerging Drugs for Parkinson's Disease," Expert Opin. Emerging Drugs., vol. 11, No. 3, pp. 403-417 (2006).

Moulignier, A., "Recepteurs Centraux de la Sérotonine Principaux Aspects Fondamentaux et fonctionnels Applications Thérapeutiques," Rev. Neurol. 150:3-15, (1994).

Moune, et al. 1997. Total synthesis of dolatrienoic acid: A subunit of dolastatin 14. J. Org. Chem., 62:3332-3339.

Mullen et al. 2000. (-)-Spiro[1-azabicyclo[2.2.2]octane-3,5'-oxazolidin-2'one], a conformationally restricted analogue of acetylcholine, is a highly selective full agonist at the α7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Nagabina, et al., "Applied technique of 1,3-dipolar cycloaddition to synthesis of new fluoroquinolones," Russian J. Organic Chem., Consultants Bureau, US, pp. 1548-1555 (1997).

Naritomi et al., "Prediction of human hepatic clearance from in vivo animal experiments and in vitro metabolic studies with liver cromosomes from animals and humans", Drug Metab. Dispos., 29(10), pp. 1316-1324 (2001).

Negibil et al., "Ablation of Serotonin 5-HT2B receptors in mice leads to abnormal cardiac structures and function", Circulation, vol. 103, pp. 2973-2979 (2001).

Negibil et al., "Serotonin 2B receptors is required for heart development", PNAS, 97(17), pp. 9508-9513 (2000).

Negibil et al., "Serotonin is a novel survival factor of cardiomyocytes: mitochondria as a target of 5-HT2B receptor signaling", FASEB J., 27(10), pp. 1373-1375 (2003).

Ng, K., Y., Chase, T., N., Colburn, R., W., and Kopin, I., J. (1970) "L-Dopa Induced Release of Cerebral Monoamines," *Science*, 170: 76-77.

Nigam, et al. 1957a. Studies with acetylenes. Part II. Some reactions of Grignard reagents with propargylic halides. Model linoleic and linolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, A., L., Farde, L., and Halidin, C. (1993) "High 5-HT2 receptor occupancy in clozapine treated patients as demonstrated by PET," *Psychopharmacology*, 110(3): 365-367.

Obach et al., The prediction of human pharmacolinetic parameters from preclinical and in Vitro metabolism data, J. Pharm. Exp. Therap., 283(1), pp. 46-58 (1997).

Ogawa, et al. 2005. Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis. European Journal of Pharmacology, 521:156-163.

Olah, et al. 1956. Notiz über die *n*-formylierung von aminen mit formylfluorid. *Chem. Ber.*, 89:2211-2212.

Old, et al. 2002. Efficient palladium-catalyzed *n*-arylation of indoles. Organic Letters, 2(10):1403-1406.

Pace, et al. "A mutant α subunit of G12 induces neoplastic transformation of Rat-1 cells," *Proc. Natl. Acad. Sci. USA* 88:7031-35 (1991).

Paiva, et al. 1988. Effects of ritanserin on sleep disturbances of dysthymic patients. *Psychopharmacology*, 96:395-399.

Parkinson Study Group (THE), "Low dose Clozapine for the treatment of drug-induced psychosis in Parkinson's disease", New Eng. J. Med., 340(10): 757-763 (1999).

Patel, et al. 2004. The highly selective 5-hydroxytryptamine (5-HT)2A receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. "Clozapine in drug-related psychosis in Parkinson's disease,", The Lancet, 353:2041-2042.

R & D Focus Drug News, vol. 10, No. 44, pp. 1-6 (Nov. 12, 2001).

R & D Focus Drug News, vol. 9, No. 3, pp. 1-12 (Jan. 24, 2000).

Read, W. T. 1922. Researches on hydantoins. Synthesis of the soporific, 4,4-phenylethyl-hydantoin(nirvanol). *J. Am. Chem. Soc.*, 44:1746-1755.

Ricci, A. 2000, *Modem Animation Methods*. New York: Wiley-VCH.

Rice, et al. 1955. Raney nickel catalyzed n-alkylation of aniline and benzidine with alcohols. *J. Am. Chem. Soc.*, 77:4052-4054.

Roberts, "Drug Evaluation: ACP-103, a 5-HT2A Receptor Inverse Agonist," Current Opin. Investig. Drugs, vol. 7, No. 7, pp. 653-660 (2006).

Rubiralta, et al., *Studies in Organic Chemistry* 43. *Piperidine: Structure, Preparation, Reactivity and Synthetic Applications of Piperidine and its Derivatives*. New York: Elsevier (1991).

Ryckmans, et al., "First dual NK1 antagonist-serotonin reuptake inhibitors: synthesis and SAR of a new class of potential antidepressants," Bioorganic & Medicinal Chemistry Letters, 261-264.

Sadzot, B., Baraban, J., M., Glennon, R., A., Lyon, R., A., Leonhardt, S., Jan, C., R., and Tietler, M. (1989) "Hallucinogenic drug interactions at human brain 5-HT2 receptors; implications for treating LSD-induced hallucinogenesis," *Psychopharmacology*, 98(4): 495-499.

Saltzman et al., "Cloning of the Human Serotonin 5-HT2 and 5-HT1C Receptor Subtypes," *Biochem. Biophys. Res. Comm.* 181:1469-1778.

Saxena, et al, "Cardiovascular Effects of Serotonin Agonists and Antagonists," *J. Cardiovascular Pharmacol*. 15: Supp. 7 (1990), pp. S17-S34.

Scheibye, et al. 1978. Studies on organophosphorus compounds XXI. The dimer of *p*-methoxyphenylthionophosphine sulfide as thiation reagent. A new route to thiocarboxamides. *Bull.* Soc. Chim. Belg., 87:229-238.

Schins, et al., Increased coronary events in depressed cardiovascular patients: 5-HT2A receptor as missing link? *Psychosomatic Medicine*, 65:729-737 (2003).

Screttas, et al. 1978. Hydrolithiation of α-olefins by a regiospecific two-step process. Transformation of alkyl phenyl sulfides to alkyllithium reagents. *J. Org. Chem.*, 43(6)1064-1071.

Scriabine, "Psychiatric Drug Discovery and Development," *CNS Drug Rev.*, vol. 9, No. 3, pp. 319-326 (2003).

Sharpley, et al. 1994. Slow wave sleep in humans: Role of 5-HT2A and 5-HT2C receptors. *Neuropharmacology*, 33(3/4):467-471.

Sica, D.A., "Alpha1-adrenergic blockers: currant usage considerations", J. Clin. Hypertension, vol. 7, pp. 757-762 (2005).

Smith, et al. 1995. New spiropiperdines as potent and selective nonpeptide tachykinin NK2 receptor antagonists. *J. Med. Chem.*, 38(19):3772-3779.

Stefancich, et al. 1984. Agenti antiinfiammatori non-steroidei: Nota III—sintesi ed attivitá analgesica-antiinfiammatoria di 4-(pirrol-1-il)-fenilacetamidi e di 4-(pirrol-1-il) fenetilamine. *Farmaco Ed. Sci.*, 39(9):752-764.

Stoner et al., "Integrated oral bioavailability protection using in vitro screening data as a selection tool in drug discovery", Int. J. Pharm., 269(1), pp. 241-249 (2004).

Stryjer, et al. 2003. Treatment of neuroleptic-induced akathisia with the 5-HT2A antagonist trazodone. *Clinical Neuropharmacology*, 26(3):137-141.

Thomas, et al. 1997. Rapid in-plate generation of benzimidazole libraries and amide formation using EEDQ, Tetrahedron Lett. 39(29):5099-5102.

Tolstikov et al., "Synthesis and Reactivity of N-substituted aminoamides, antiarrhythmic and local anaesthetic activity" *Russian Chemical Reviews* 60(4):420434 (1991).

Tsukamoto, et al. 1995. Synthesis and structure-activity studies of a series of 1-oxa-2,8-diazaspiro[4.5]decan-3-ones and related compounds as M1 muscarinic agonists. *Chem. Pharm. Bull.*, 43(9):1523-1529.

Vallar et al., "Aletered G3 and adenylate cyclase activity in human GH-secreting pituitary adenomas", Nature 330:556-58 (1987).

Van Laar, et al. 2001. Subchronic effects of the GABA-agonist lorazepam and the 5-HT2A/2C antagonist ritanserin on driving performance, slow wave sleep and daytime sleepiness in healthy volunteers. *Psychophannacology*, 154:189-197.

Vanover, et al., "ACP-103, A 5-HT2A Receptor Inverse Agonist, A Novel Potential Treatment For Psychosis," *Schizophrenia Research*, vol. 60, No. 1, Supp. [S], p. 317 (2003).

Vanover, et al., "ACP-103, A 5-HT2A Receptor Inverse Agonist: Safety, Tolerability and Pharmacokinetics in Healthy Volunteers," *International J. Neuropsychopharmacology*, vol. 7, No. Supp. 2, pp. S253 (2004).

Vanover, et al., "Pharmacological and Behavioral Profile of N-(4-fluorophenylmethyl)-N-(1-methylpiperidin'4-yl)-N'-(4-(2-methylpropyloxy)phenylmethyl) Carbamide (2R, 3R)-Dihydroxybutanedioate (2:!) (ACP-103), a Novel 5-Hydroxytrptamine 2A Receptor Inverse Agonist," *J. Pharmacology & Experimental Therapeutics*, vol. 317, No. 2, pp. 910-918 (2006).

Vanover, et al., "Pharmacological Characterization of AC-90179 [2-(4-Methoxy-phenyl)-*N*-(4-methyl-benzyl)-*N*-(1-methyl-piperidiny-4-yl)-acetamide Hydrochloride]: A Selective Serotonin 2A Receptor Inverse Agonist," *J. Pharmacology & Experimental Therapeutics*, vol. 310, No. 3, pp. 943-951 (2004).

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem.*, 67(1):106-111.

Wade, et al. 2000. Application of base cleavable safety catch linkers to solid phase library production. *J. Comb. Chem.*, 2(3):266-275.

Weiner, D., M., Burstein, E., S., Nash, N., Croston, G., E., Currier, E., A., Vanover, K., E., Harvey, S., C., Donohue, E., Hansen, H., C., Andersson, C., M., Spalding, T., A., Gibson, D., F., Krebs-Thomson, K., Powell, S., B., Geyer, M., A., Hacksell, U., and Brann, M., R. (2001) "5-Hydroxytryptamine2A Receptor Inverse Agonists as Antipsychotics," *J Pharmacol Exp Ther.*, 299(1):268-76.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wirshing et al., "Novel antipsychotics: comparison of weight gain liabilities", J. Clin. Psychiatry, 21(6), pp. 579-587 (1999).

Wolf, V. V. 1952. Über alkin-amine I. Aryl-propargyl-amine. *Liebigs Ann. Chem.*, 576:35-45.

Wolfe, et al. 1996. An improved catalyst system for aromatic carbon-nitrogen bond formation: The possible involvement of bis(phosphine) palladium complexes as key intermediates. *J. Am. Chem. Soc.*, 118:7215-7216.

Yamada, et al. 1998. Alternative synthesis of TTF donors with a dioxolane ring, and synthesis of their dithiolane and oxathiolane analogues. *Tetrahedron Letters*, 39:7709-7712.

Yang, et al. 1999. Palladium-catalyzed amination of aryl halides and sulfonates. *Journal of Organometallic Chemistry*, 576:125-146.

Yasuhara, et al. 2000. An activated phosphate for an efficient amide and peptide coupling reagent. *J. Chem. Soc., Perkin Trans.* 1, 17:2901-2902.

Yin, et al. 2002. Pd-catalyzed intermolecular amidation of aryl halides: The discovery that xantphos can be trans-chelating in a palladium complex. *J. Am. Chem. Soc.*, 124:6043-6048.

Yoshida, K. et al. "Marked Improvement of Tardive Dystonia After Replacing Haloperidol with Risperidone in a Schizophrenic Patient." (Clinical Neuropharmacology), 1998, vol. 21, No. 1: 68-69.

U.S.P.T.O. Non-Final Office Action dated Jul. 11, 2008, in U.S. Appl. No. 10/759,561.

U.S.P.T.O. Non-Final Office Action dated Jan. 6, 2009, in U.S. Appl. No. 10/759,561.

U.S.P.T.O. Non-Final Office Action dated Oct. 10, 2007, in U.S. Appl. No. 10/759,561.

U.S.P.T.O. Notice of Allowance dated Jun. 17, 2009, in U.S. Appl. No. 10/759,561.

Official communication in European Patent Application No. 04702584.6-2123, dated Apr. 5, 2006.

Official communication in European Patent Application No. 04702584.6-2123, dated Feb. 23, 2007.

U.S.P.T.O. Non-Final Office Action dated Nov. 1, 2007, in U.S. Appl. No. 10/850,819.

U.S.P.T.O. Non-Final Office Action dated May 2, 2008, in U.S. Appl. No. 10/850,819.

U.S.P.T.O. Non-Final Office Action dated Jan. 29, 2009, in U.S. Appl. No. 10/850,819.

U.S.P.T.O. Final Office Action dated Sep. 14, 2009, in U.S. Appl. No. 10/850,819.

U.S.P.T.O. Non-Final Office Action dated Dec. 17, 2009, in U.S. Appl. No. 10/850,819.

U.S.P.T.O. Notice of Allowance dated Jun. 23, 2010, in U.S. Appl. No. 10/850,819.

SELECTIVE SEROTONIN RECEPTOR INVERSE AGONISTS AS THERAPEUTICS FOR DISEASE

This application claims the benefit of, and is a continuation application of, U.S. Ser. No. 10/854,035, filed May 24, 2004, now abandoned which is a continuation-in-part of U.S. Ser. No. 10/850,819, filed May 21, 2004. The contents of each of which are incorporated by reference herein in their entirety.

BACKGROUND OF THE INVENTION

1. Field of the Invention

The present invention relates to novel combinations of compounds that are effective as therapeutic agents in the treatment of depression, mania, or social phobia, and other psychotic disorders. The combinations include inverse serotonin agonists and another antidepressant, anti-maniac, anti-phobia, or antipsychotic agent.

2. Description of the Related Art

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission*, 1982; Boullin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine*, 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106S-115S (1999); Barnes & Sharp, *Neuropharmacology*, 38:1083-1152 (1999); Glennon, *Neurosci. Biobehavioral Rev.*, 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

We have recently elucidated an important aspect of 5-HT2A receptor function by applying the Receptor Selection and Amplification Technology (U.S. Pat. No. 5,707,798, 1998; Chem. Abstr. 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (U.S. Patent Application Ser. No. 60/103,317, herein incorporated by reference). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinico-pharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptors subtypes, especially dopamine D2 receptors. Such compounds may be useful in the treatment of human disease (e.g., as anti-psychotics), and may avoid the adverse side effects associated with non-selective receptor interactions.

SUMMARY OF THE INVENTION

Disclosed herein is a pharmaceutical composition comprising: a first compound selected from the group consisting of an inverse agonist of a serotonin receptor, an antagonist of a serotonin receptor, and pharmaceutically acceptable salts thereof; and a second compound selected from the group consisting of a SSRI, a SNRI, a MAO-I, a TCA, an antipsychotic agent, a norepinephrine reuptake inhibitor, a dopamine agonist, an anti-insomnia drug, an anti-manic drug, an anti-phobia drug, the compound of Formula (II)

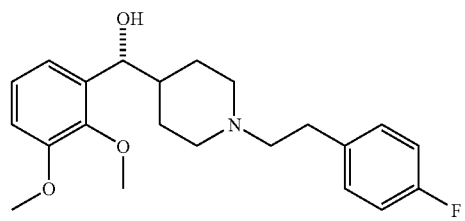

(II)

and pharmaceutically acceptable salts thereof. In some embodiments, the serotonin receptor is a 5HT2A receptor. In some embodiments, the first compound is a compound of Formula (I):

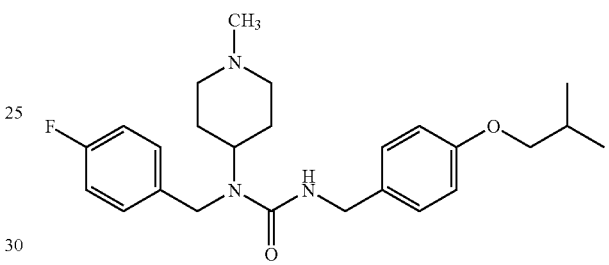

(I)

In some embodiments, the first compound is a compound of Formula (H):

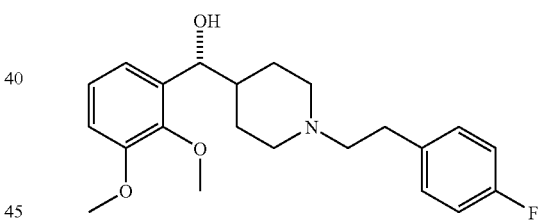

(II)

and the second compound selected from the group consisting of a SSRI, a SNRI, a MAO-I, a TCA, an antipsychotic agent, a norepinephrine reuptake inhibitor, a dopamine agonist, an anti-insomnia drug, an anti-manic drug, an anti-phobia drug. In some embodiments, the SSRI is selected from the group consisting of bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. In some embodiments, the SNRI is selected from the group consisting of citalopram (Celexa), dulexetine, escitalopram (Lexapro), fluvoxamine (Luvox), and venfalaxine (effexor). In some embodiments, the MAO-I is selected from the group consisting of tranylcypromine (Parnate), phenelzine (Nardil), maprotiline, and isocarboxazid (Marplan). In some embodiments, the TCA is selected from the group consisting of amitryptiline (Norpramine), amoxapineclomipramine (Anafranil), desipramine, doxepin (Sinequan), imipramine (Tofranil), maprotiline, (Elavil), protryptiline, and trimipramine. In some embodiments, the antipsychotic agent is selected from the group consisting of a phenothiazine, a phenylbutylpiperadine, a debenzapine, a benzisoxidil, and a salt of lithium. In some embodiments, the phenothiazine is selected from the group consisting of chlorpromazine (Thorazine®), mesoridazine (Serentil®), prochlorperazine (Compazine®), and thioridazine (Mellaril In some embodiments, the phenylbutylpiperadine is selected from the group consisting of haloperidol (Haldol®) and pimozide (Orap®). In some embodiments, the debenzapine is selected from the group consisting of clozapine (Clozaril®), loxapine (Loxitane®), olanzapine (Zyprexa®), and quetiapine (Seroquel®). In some embodiments, the benzisoxidil is selected from the group consisting of resperidone (Resperidal®) and ziprasidone (Geodon®). In some embodiments, the salt of lithium is lithium carbonate. In some embodiments, the antipsychotic agent is selected from the group consisting of Aripiprazole (Abilify), Etrafon Haldol, Inapsine, Mellaril, Moban, Navane, Permitil, Prolixin, Phenergan, Reglan, Risperdal, Stelazine, Taractan, Triavil, and Trilafon. In some embodiments, the norepinephrine reuptake inhibitor is selected from the group consisting of thionisoxetine and reboxetine. In some embodiments, the dopamine agonist is selected from the group consisting of sumatriptan, almotriptan, naratriptan, frovatriptan, rizatriptan, zomitriptan, cabergoline, amantadine, lisuride, pergolide, ropinirole, pramipexole, and bromocriptine. In some embodiments, the anti-insomnia drug is selected from the group consisting of alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. In some embodiments, the anti-manic drug is selected from the group consisting of divalproex (Depakote), lithium carbonate (Eskalith), and lithium citrate. In some embodiments, the anti-phobia drug is D-cycloserine. In some embodiments, the pharmaceutical composition further comprises physiologically acceptable carrier, diluent, or excipient, or a combination thereof. In one embodiment, the first compound is the compound of Formula (I):

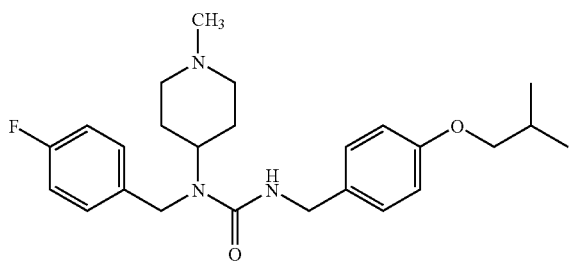

(I)

and the second compound is fluoxetine.

Also disclosed herein is a method of treating a disorder in a patient, the disorder selected from the group consisting of depression, mania, social phobia, psychosis, and a neuropsychiatric disorder, the method comprising: identifying a patient in need of the treatment, and administering to the patient a therapeutically effective amount of a combination of a first compound and a second compound, the first compound selected from the group consisting of an inverse agonist of a serotonin receptor, an antagonist of a serotonin receptor, and pharmaceutically acceptable salts thereof, as described above and the second compound selected from the group consisting of a SSRI, a SNRI, a MAO-I, a TCA, an antipsychotic agent, a norepinephrine reuptake inhibitor, a dopamine agonist, an anti-insomnia drug, an anti-manic drug, an anti-phobia drug, the compound of Formula (II):

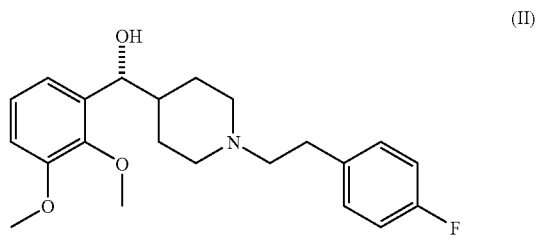

(II)

and pharmaceutically acceptable salts thereof, as described above. In some embodiments, the neuropsychiatric disorder is selected from the group consisting of schizophrenia and related idiopathic psychoses, anxiety, sleep disorders, appetite disorders, affective disorders, Tourette's Syndrome, drug-induced psychoses, and psychoses secondary to neurodegenerative disorders. In some embodiments, the affective disorders are selected from the group consisting of major depression, bipolar disorder, and depression with psychotic features. In some embodiments, the neurodegenerative disorders are selected from the group consisting of Alzheimer's and Huntington's Disease. In one embodiment, the disorder is depression, the first compound is the compound of Formula (I):

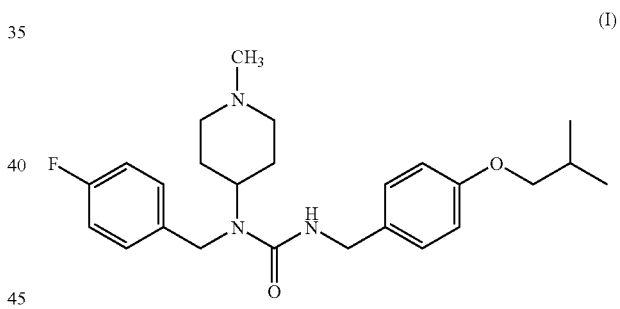

(I)

and the second compound is fluoxetine.

Also disclosed herein is a pharmaceutical composition comprising the compound of Formula (I):

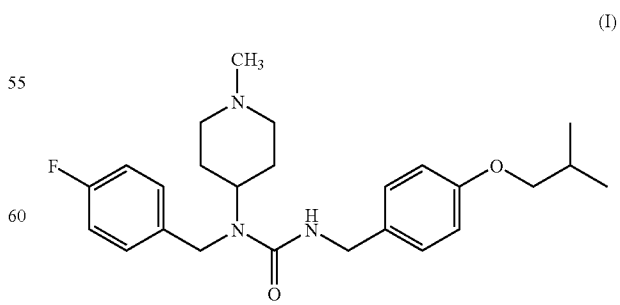

(I)

and a compound selected from the group consisting of a SSRI, a SNRI, a MAO-I, a TCA, an antipsychotic agent, a norepinephrine reuptake inhibitor, a dopamine agonist, an anti-insomnia drug, an anti-manic drug, an anti-phobia drug, the compound of Formula (II):

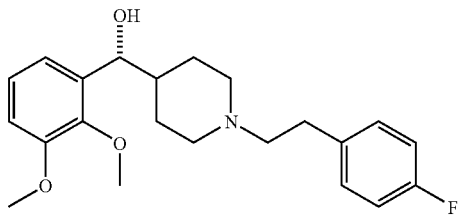

(II)

and pharmaceutically acceptable salts thereof. In some embodiments, the SSRI is selected from the group consisting of bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. In some embodiments, the SNRI is selected from the group consisting of citalopram (Celexa), dulexetine, escitalopram (Lexapro), fluvoxamine (Luvox), and venfalaxine (effexor). In some embodiments, the MAO-I is selected from the group consisting of tranylcypromine (Parnate), phenelzine (Nardil), maprotiline, and isocarboxazid (Marplan). In some embodiments, the TCA is selected from the group consisting of amitryptiline (Norpramine), amoxapineclomipramine (Anafranil), desipramine, doxepin (Sinequan), imipramine (Tofranil), maprotiline, (Elavil), protryptiline, and trimipramine. In some embodiments, the antipsychotic agent is selected from the group consisting of a phenothiazine, a phenylbutylpiperadine, a debenzapine, a benzisoxidil, and a salt of lithium. In some embodiments, the phenothiazine is selected from the group consisting of chlorpromazine (Thorazine®), mesoridazine (Serentil®), prochlorperazine (Compazine®), and thioridazine (Mellaril In some embodiments, the phenylbutylpiperadine is selected from the group consisting of haloperidol (Haldol®) and pimozide (Orap®). In some embodiments, the debenzapine is selected from the group consisting of clozapine (Clozaril®), loxapine (Loxitane®), olanzapine (Zyprexa®), and quetiapine (Seroquel®). In some embodiments, the benzisoxidil is selected from the group consisting of resperidone (Resperidal®) and ziprasidone (Geodon®). In some embodiments, the salt of lithium is lithium carbonate. In some embodiments, the antipsychotic agent is selected from the group consisting of Aripiprazole (Abilify), Etrafon Haldol, Inapsine, Mellaril, Moban, Navane, Permitil, Prolixin, Phenergan, Reglan, Risperdal, Stelazine, Taractan, Triavil, and Trilafon. In some embodiments, the norepinephrine reuptake inhibitor is selected from the group consisting of thionisoxetine and reboxetine. In some embodiments, the dopamine agonist is selected from the group consisting of sumatriptan, almotriptan, naratriptan, frovatriptan, rizatriptan, zomitriptan, cabergoline, amantadine, lisuride, pergolide, ropinirole, pramipexole, and bromocriptine. In some embodiments, the anti-insomnia drug is selected from the group consisting of alprazolam (Xanax), chlordiazepoxide (Librium, Limbitrol), clorazepate (Tranxene), estazolam (ProSom), flurazepam (Dahnane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. In some embodiments, the anti-manic drug is selected from the group consisting of divalproex (Depakote), lithium carbonate (Eskalith), and lithium citrate. In some embodiments, the anti-phobia drug is D-cycloserine. In some embodiments, the pharmaceutical composition further comprises physiologically acceptable carrier, diluent, or excipient, or a combination thereof. In some embodiments, a method is provided for treating a disorder in a patient, the disorder selected from the group consisting of depression, mania, social phobia, psychosis, and a neuropsychiatric disorder, the method comprising: identifying a patient in need of the treatment, and administering to the patient a therapeutically effective amount of the composition described above.

Also disclosed herein is a pharmaceutical composition comprising a compound of Formula (II):

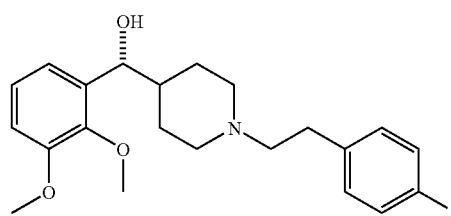

(II)

and a compound selected from the group consisting of a SSRI, a SNRI, a MAO-I, a TCA, an antipsychotic agent, a norepinephrine reuptake inhibitor, a dopamine agonist, an anti-insomnia drug, an anti-manic drug, an anti-phobia drug, and pharmaceutically acceptable salts thereof. In some embodiments, the SSRI is selected from the group consisting of bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. In some embodiments, the SNRI is selected from the group consisting of citalopram (Celexa), dulexetine, escitalopram (Lexapro), fluvoxamine (Luvox), and venfalaxine (effexor). In some embodiments, the MAO-I is selected from the group consisting of tranylcypromine (Parnate), phenelzine (Nardil), maprotiline, and isocarboxazid (Marplan). In some embodiments, the TCA is selected from the group consisting of amitryptiline (Norpramine), amoxapineclomipramine (Anafranil), desipramine, doxepin (Sinequan), imipramine (Tofranil), maprotiline, (Elavil), protryptiline, and trimipramine. In some embodiments, the antipsychotic agent is selected from the group consisting of a phenothiazine, a phenylbutylpiperadine, a debenzapine, a benzisoxidil, and a salt of lithium. In some embodiments, the phenothiazine is selected from the group consisting of chlorpromazine (Thorazine®), mesoridazine (Serentil®), prochlorperazine (Compazine®), and thioridazine (Mellaril In some embodiments, the phenylbutylpiperadine is selected from the group consisting of haloperidol (Haldol®) and pimozide (Orap®). In some embodiments, the debenzapine is selected from the group consisting of clozapine (Clozaril®), loxapine (Loxitane®), olanzapine (Zyprexa®), and quetiapine (Seroquel®). In some embodiments, the benzisoxidil is selected from the group consisting of resperidone (Resperidal®) and ziprasidone (Geodon®). In some embodiments, the salt of lithium is lithium carbonate. In some embodiments, the antipsychotic agent is selected from the group consisting of Aripiprazole (Abilify), Etrafon Haldol, Inapsine, Mellaril, Moban, Navane, Permitil, Prolixin, Phenergan, Reglan, Risperdal, Stelazine, Taractan, Triavil, and Trilafon. In some embodiments, the norepinephrine reuptake inhibitor is selected from the group consisting of thionisoxetine and reboxetine. In some embodiments, the dopamine agonist is selected from the group consisting of sumatriptan, almotriptan, naratriptan, frovatriptan, rizatriptan, zomitriptan, cabergoline, amantadine, lisuride, pergolide, ropinirole, pramipexole, and bromocriptine. In some embodiments, the anti-insomnia drug is selected from the group consisting of alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. In some embodiments, the anti-manic drug is selected from the group consisting of divalproex (Depakote), lithium carbonate (Eskalith), and lithium citrate. In some embodiments, the anti-phobia drug is D-cycloserine. In some embodiments, the pharmaceutical composition further comprises physiologically acceptable carrier, diluent, or excipient, or a combination thereof. In some embodiments, a method is provided for treating a disorder in a patient, the disorder selected from the group consisting of depression, mania, social phobia, psychosis, and a neuropsychiatric disorder, the method comprising: identifying a patient in need of the treatment, and administering to the patient a therapeutically effective amount of the composition described above.

DETAILED DESCRIPTION OF THE PREFERRED EMBODIMENT

Definitions

For the purpose of the current disclosure, the following definitions shall in their entireties be used to define technical terms, and shall also, in their entireties, be used to define the scope of the composition of matter for which protection is sought in the claims.

"Constitutive activity" is defined as the elevated basal activity of a receptor that is independent of the presence of an agonist. Constitutive activity of a receptor may be measured using a number of different methods, including cellular (e.g., membrane) preparations (see, e.g., Barr &. Manning, *J. Biol. Chem.* 272:32979-87 (1997)), purified reconstituted receptors with, or without the associated G-protein in phospholipid vesicles (Cerione et al., *Biochemistry* 23:4519-25 (1984)), and functional cellular assays (U.S. patent application Ser. No. 60/103,317) or any other method known in the art.

"Agonist" is defined as a compound that increases the basal activity of a receptor when it contacts the receptor.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

An "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The "5-HT2A receptor" is defined as a receptor, having an activity corresponding to the activity of the human serotonin receptor subtype, which was characterized through molecular cloning and pharmacology as detailed in Saltzman et al., *Biochem. Biophys. Res. Comm.* 181:1469-78; and Julius et al., *Proc. Natl. Acad. Sci. USA* 87:928-932, the disclosures of which are incorporated herein by reference in their entireties.

The term "subject" refers to an animal, preferably a mammal, most preferably a human, who is the object of treatment, observation or experiment.

"Selective" is defined as a property of a compound whereby an amount of the compound sufficient to effect a desired response from a particular receptor type, subtype, class or subclass with significantly less or substantially little or no effect upon the activity other receptor types. For example, a selective compound may have at least a 10-fold greater effect on activity of the desired receptor than on other receptor types. In some cases, a selective compound may have at least a 20-fold greater effect on activity of the desired receptor than on other receptor types, or at least a 50-fold greater effect, or at least a 100-fold greater effect, or at least a 1000-fold greater effect, or at least a 10,000-fold greater effect, or at least a 100,000-fold greater effect, or more than a 100,000-fold greater effect. "Selectivity" or "selective," as an inverse agonist is understood as a property of the compound of the invention whereby an amount of compound that effectively inversely agonizes the 5-HT2A receptor, and thereby decreases its activity, causes little or no inverse agonistic or antagonistic activity at other, related or unrelated, receptors. In particular, in one embodiment, a compound has surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. In one embodiment, the compound is also selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with drugs hitherto suggested for this purpose.

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological, and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission*, 1982; Botillin, *Serotonin In Men-* tal Abnormalities 1:316 (1978); Barchas, et al., Serotonin and Behavior, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et at, The *Peripheral Actions of 5-Hydroxytryptamine*, 246 (1989); Saxena, et at, *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s). Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106S-115S (1999); Barnes & Sharp, *Neuropharmacology*, 38:1083-1152 (1999); Glennon, *Neurosci. Biobehavioral Rev.*, 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

In one aspect, the present invention relates to a method of treating depression in a patient comprising identifying a patient in need thereof, and administering to the patient a therapeutically effective amount of a first compound in combination with a therapeutically effective amount of a second compound.

In another aspect, the present invention relates to a method of treating mania in a patient comprising identifying a patient in need thereof, and administering to the patient a therapeutically effective amount of a first compound in combination with a therapeutically effective amount of a second compound.

In yet another aspect, the present invention relates to a method of treating social phobia in a patient comprising identifying a patient in need thereof, and administering to the patient a therapeutically effective amount of a first compound in combination with a therapeutically effective amount of a second compound.

In a further aspect, the present invention relates to a method of treating psychosis in a patient comprising identifying a patient in need thereof, and administering to the patient a therapeutically effective amount of a first compound in combination with a therapeutically effective amount of a second compound.

In another aspect, the present invention relates to a method of treating a neuropsychiatric disorder in a patient comprising identifying a patient in need thereof, and administering to said patient a therapeutically effective amount of a first compound in combination with a therapeutically effective amount of a second compound. In some embodiments, the neuropsychiatric disorder is selected from the group consisting of schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such Alzheimer's or Huntington's Disease.

The term "therapeutically effective amount" as used herein means an amount of an active compound or pharmaceutical agent that elicits the biological or medicinal response in a tissue, system, animal or human that is being sought by a researcher, veterinarian, medical doctor or other clinician, which includes alleviation, amelioration, or lessening of the symptoms of the disease being treated, or prevents or slows the progress of the disease or increase of the symptoms.

In certain embodiments, the patient may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the patient is a human.

In some embodiments, the first compound in the above methods is an inverse agonist selective for a serotonin receptor. In certain embodiments, the serotonin receptor is a 5HT2A receptor, while in other embodiments the serotonin receptor is a 5HT2C receptor. In other embodiments, the inverse agonists binds to a 5HT2A receptor and a 5HT2C receptor.

In some embodiments, the first compound is a compound of formula (III)

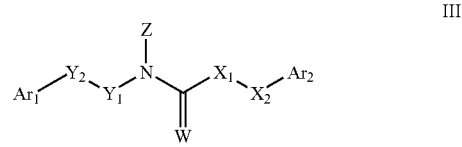

III where
Z is

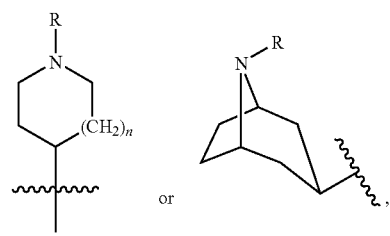

or wherein R is a hydrogen, a cyclic or straight-chained or branched acyclic organyl group, a lower hydroxyalkyl group, a lower aminoalkyl group, or an aralkyl or heteroaralkyl group; and n is 1;

$X_1$ is methylene, vinylene, or an NH or N(lower alkyl) group; and $X_2$ is methylene; or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups, provided that $Ar_1$ and $Ar_2$ are not simultaneously unsubstituted phenyl; and W is oxygen; or a pharmaceutically acceptable salt or prodrug thereof.

In other embodiments, the first compound is a compound disclosed in U.S. Patent Application Publication Serial No. 2002/0004513 A1, published on Jan. 10, 2002, by Andersson et al., and entitled "AZACYCLIC COMPOUNDS," which is the publication of the U.S. application Ser. No. 09/800,096, or in U.S. Patent Application Publication Serial No. 2003/0220316 A1, published on Nov. 27, 2003, by Andersson et al., and entitled "AZACYCLIC COMPOUNDS," which is the publication of the U.S. application Ser. No. 10/409,782, or in U.S. application Ser. No. 10/802,970, filed on Mar. 16, 2004, by Andersson et al., and entitled "AZACYCLIC COMPOUNDS," the entire disclosure of all of which is hereby incorporated by reference herein in their entirety, including any drawings.

In another embodiment, the first compound is N-(1-methylpiperidin-4-yl)-N-(4-fluorophenylmethyl)-N'-(4-(2-methylpropyloxy)phenylmethyl)carbamide, which is the compound of Formula (I):

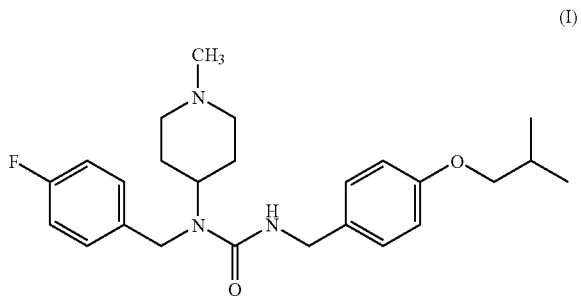

(I)

In another embodiment, the first compound in the above methods is an antagonist selective for a serotonin receptor. In certain embodiments, the serotonin receptor is a 5HT2A receptor, while in other embodiments the serotonin receptor is a 5HT2C receptor. In other embodiments, the antagonists binds to a 5HT2A receptor and a 5HT2C receptor.

In some embodiments, the second compound in the above methods is a selective serotonin reuptake inhibitor (SSRI). Examples of SSRIs include, but are not limited to, bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. Any other SSRI currently known or later developed are within the scope of the present disclosure.

In other embodiments, the second compound in the above methods is a serotonin/norepinephrine reuptake inhibitor (SNRI). Examples of SNRIs include, but are not limited to, citalopram (Celexa), duloxetine, escitalopram (Lexapro), fluvoxamine (Luvox), and venfalaxine (effexor). Any other SNRI currently known or later developed are within the scope of the present disclosure.

In further embodiments, the second compound in the above methods is a monoamine oxidase inhibitor (MAO-I). Examples of MAO-Is include, but are not limited to, tranylcypromine (Pamate), phenelzine (Nardil), maprotiline, and isocarboxazid (Marplan). Any other MAO-I currently known or later developed are within the scope of the present disclosure.

In yet other embodiments, the second compound in the above methods is a tricyclic antidepressant (TCA). Examples of TCAs include, but are not limited to, amitryptiline (Norpramine), amoxapineclomipramine (Anafranil), desipramine, doxepin (Sinequan), imipramine (Tofranil), maprotiline, (Elavil), protryptiline, and trimipramine. Any other TCA currently known or later developed are within the scope of the present disclosure.

In some other embodiments, the second compound in the above methods is a compound selected from aripiprazole (Abilify), clozapine, fluoxetine/olanzapine (Symbyax), olanzapine (Zyprexa), quetiapine (Seroquel), risperidone (Risperdal), valproic acid (Depakote), and ziprasidone (Geodon). Any other atypical antidepressant currently known or later developed are within the scope of the present disclosure.

In some embodiments, the second compound in the above methods is a compound selected from chlorpromazine (Thorazine®), mesoridazine (Serentil®), prochlorperazine (Compazine®), thioridazine (Mellaril®), haloperidol (Haldol®), pimozide (Orap®), clozapine (Clozaril®), loxapine (Loxitane®), olanzapine (Zyprexa®), quetiapine (Seroquel®), resperidone (Resperidal®), ziprasidone (Geodon®), lithium carbonate, Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa.

In some embodiments, the second compound in the above methods is an antipsychotic agent. The antipsychotic agent may be selected from the group consisting of a phenothiazine, phenylbutylpiperadine, debenzapine, benzisoxidil, and salt of lithium. The phenothiazine group of compounds may be selected from the group consisting of chlorpromazine (Thorazine®), mesoridazine (Serentil®), prochlorperazine (Compazine®), and thioridazine (Mellaril®). The phenylbutylpiperadine group of compounds may be selected from the group consisting of haloperidol (Haldol®), and pimozide (Orap®). The debenzapine group of compounds may be selected from the group consisting of clozapine (Clozaril®), loxapine (Loxitane®), olanzapine (Zyprexa®) and quetiapine (Seroquel®). The benzisoxidil group of compounds may be selected from the group consisting of resperidone (Resperidal®) and ziprasidone (Geodon®). The salt of lithium may be lithium carbonate. In some embodiments, the antipsychotic agent may be selected from the group consisting of Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa, or pharmaceutically acceptable salts thereof.

In other embodiments, the second compound in the above methods is a norepinephrine reuptake inhibitor. The norepinephrine reuptake inhibitor is selected from the group consisting of thionisoxetine and reboxetine.

In further embodiments, the second compound in the above methods is a dopamine agonist. The dopamine agonist may be selected from the group consisting of sumatriptan, almotriptan, naratriptan, frovatriptan, rizatriptan, zomitriptan, cabergoline, amantadine, lisuride, pergolide, ropinirole, pramipexole, and bromocriptine.

In yet another embodiment, the second compound in the above methods is an anti-insomnia drug. Examples of anti-insomnia drugs include, but are not limited to, alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. Any other anti-insomnia drug currently known or later developed are within the scope of the present disclosure.

In other embodiments, the second compound in the above methods is an anti-manic drug. Examples of anti-manic drugs include, but are not limited to, divalproex (Depakote), lithium carbonate (Eskalith), and lithium citrate. Any other anti-manic drug currently known or later developed are within the scope of the present disclosure.

In some embodiments, the second compound in the above methods is an anti-phobia drug. An example of anti-phobia drugs includes, but is not limited to, D-cycloserine. Those of skill in the art recognize that some of the other drugs disclosed herein also work as anti-phobia drugs. Any other anti-manic drug currently known or later developed are within the scope of the present disclosure.

In other embodiments, the first or second compound in the above methods is a serotonin 2A antagonist. The serotonin 2A antagonist may be M 100,907 or an analog thereof. By "M 100,907," it is meant the compound of Formula II.

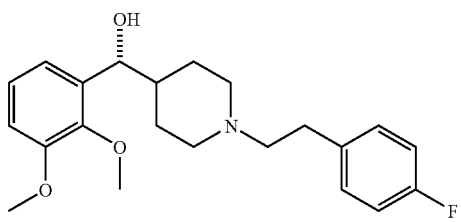

(II)

In some embodiments, a first compound of Formula (I) is administered in combination with a second compound of Formula (II). In other embodiments, a first compound of Formula (II) is administered in combination with a second compound selected from the group consisting of a SSRI including but not limited to bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine; a SNRI including but not limited to citalopram (Celexa), dulexetine, escitalopram (Lexapro), fluvoxamine (Luvox), and venfalaxine (effexor); a MAO-I including but are not limited to tranylcypromine (Parnate), phenelzine (Nardil), maprotiline, and isocarboxazid (Marplan); a TCA including but not limited to amitryptiline (Norpramine), amoxapineclomipramine (Anafranil), desipramine, doxepin (Sinequan), imipramine (Tofranil), maprotiline, (Elavil), protryptiline, and trimipramine; aripiprazole (Abilify); clozapine; fluoxetine/olanzapine (Symbyax); olanzapine (Zyprexa); quetiapine (Seroquel); risperidone (Risperdal); valproic acid (Depakote); ziprasidone (Geodon); chlorpromazine (Thorazine®); mesoridazine (Serentil®); prochlorperazine (Compazine®); thioridazine (Mellaril®); haloperidol (Haldol®); pimozide (Orap®); clozapine (Clozaril®); loxapine (Loxitane®); olanzapine (Zyprexa®); quetiapine (Seroquel®); resperidone (Resperidal®); ziprasidone (Geodon®); lithium carbonate; Aripiprazole (Abilify); Clozapine; Clozaril; Compazine; Etrafon; Geodon; Haldol; Inapsine; Loxitane; Mellaril; Moban; Navane; Olanzapine (Zyprexa); Orap; Permitil; Prolixin; Phenergan; Quetiapine (Seroquel); Reglan; Risperdal; Serentil; Seroquel; Stelazine; Taractan; Thorazine; Triavil; Trilafon; Zyprexa; an antipsychotic agent including but not limited to a phenothiazine such as chlorpromazine (Thorazine®), mesoridazine (Serentil®), prochlorperazine (Compazine®), and thioridazine (Mellaril®), a phenylbutylpiperadine such as haloperidol (Haldol®) and pimozide (Orap®), a debenzapine such as clozapine (Clozaril®), loxapine (Loxitane®), olanzapine (Zyprexa®) and quetiapine (Seroquel®), a benzisoxidil such as resperidone (Resperidal®) and ziprasidone (Geodon®), a salt of lithium such as lithium carbonate, Aripiprazole (Abilify), Etrafon Haldol, Inapsine, Mellaril, Moban, Navane, Permitil, Prolixin, Phenergan, Reglan, Risperdal, Stelazine, Taractan, Triavil, and Trilafon; a norepinephrine reuptake inhibitor including but not limited to thionisoxetine and reboxetine; a dopamine agonist including but not limited to sumatriptan, almotriptan, naratriptan, frovatriptan, rizatriptan, zomitriptan, cabergoline, amantadine, lisuride, pergolide, ropinirole, pramipexole, and bromocriptine; an anti-insomnia drug including but not limited to alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs; an anti-manic drug including but not limited to divalproex (Depakote), lithium carbonate (Eskalith), and lithium citrate; an anti-phobia drug including but not limited to D-cycloserine; and pharmaceutically acceptable salts thereof.

In some embodiments, the administering step in the above methods comprises administering the first compound and the second compound simultaneously. These embodiments include those in which the first compound and the second compound are in the same administrable composition, i.e., a single tablet, pill, or capsule, or a single solution for intravenous injection, or a single drinkable solution, or a single dragee formulation or patch, contains both compounds. The embodiments also include those in which each compound is in a separate administrable composition, but the patient is directed to take the separate compositions nearly simultaneously, i.e., one pill is taken right after the other or that one injection of one compound is made right after the injection of another compound, etc.

In other embodiments the administering step comprises administering one of the first compound and the second compound first and then administering the other one of the first compound and the second compound. In these embodiments, the patient may be administered a composition comprising one of the compounds and then at some time, a few minutes or a few hours, later be administered another composition comprising the other one of the compounds. Also included in these embodiments are those in which the patient is administered a composition comprising one of the compounds on a routine or continuous basis while receiving a composition comprising the other compound occasionally.

In another aspect, the present invention relates to a pharmaceutical composition comprising a first compound and a second compound.

In some embodiments, the first compound in the above pharmaceutical composition is an inverse agonist selective for a serotonin receptor. In certain embodiments, the serotonin receptor is a 5HT2A receptor, while in other embodiments the serotonin receptor is a 5HT2C receptor. In other embodiments, the inverse agonists binds to a 5HT2A receptor and a 5HT2C receptor.

In some embodiments, the first compound is a compound of formula (III)

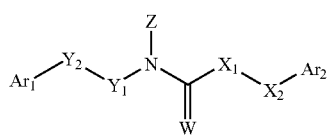

where
Z is

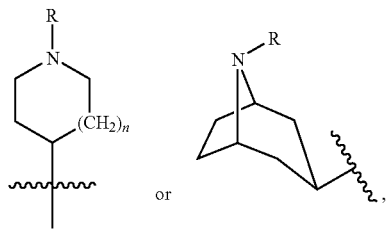

wherein R is a hydrogen, a cyclic or straight-chained or branched acyclic organyl group, a lower hydroxyalkyl group, a lower aminoalkyl group, or an aralkyl or heteroaralkyl group; and n is 1;

$X_1$ is methylene, vinylene, or an NH or N(lower alkyl) group; and $X_2$ is methylene; or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups, provided that $Ar_1$ and $Ar_2$ are not simultaneously unsubstituted phenyl; and W is oxygen; or a pharmaceutically acceptable salt or prodrug thereof.

In other embodiments, the first compound is a compound disclosed in U.S. Patent Application Publication Serial No. 2002/0004513 A1, published on Jan. 10, 2002, by Andersson et al., and entitled "AZACYCLIC COMPOUNDS," which is the publication of the U.S. application Ser. No. 09/800,096, or in U.S. Patent Application Publication Serial No. 2003/0220316 A1, published on Nov. 27, 2003, by Andersson et al., and entitled "AZACYCLIC COMPOUNDS," which is the publication of the U.S. application Ser. No. 10/409,782, or in U.S. application Ser. No. 10/802,970, filed on Mar. 16, 2004, by Andersson et al., and entitled "AZACYCLIC COMPOUNDS," the entire disclosures of all of which are hereby incorporated by reference herein in their entirety, including any drawings.

In another embodiment, the first compound is N-(1-methylpiperidin-4-yl)-N-(4-fluorophenylmethyl)-N'-(4-(2-methylpropyloxy)phenylmethyl)carbamide, which is the compound of Formula (I):

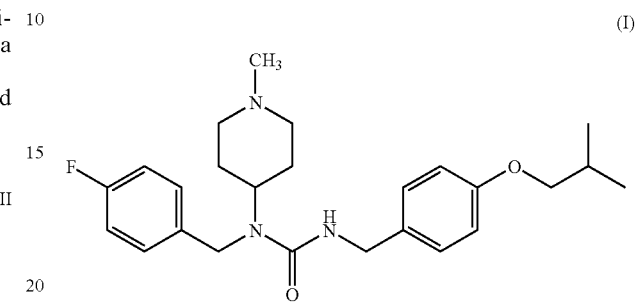

In another embodiment, the first compound in the above pharmaceutical composition is an antagonist selective for a serotonin receptor. In certain embodiments, the serotonin receptor is a 5HT2A receptor, while in other embodiments the serotonin receptor is a 5HT2C receptor. In other embodiments, the antagonists binds to a 5HT2A receptor and a 5HT2C receptor.

In some embodiments, the second compound in the above pharmaceutical composition is a selective serotonin reuptake inhibitor (SSRI). Examples of SSRIs include, but are not limited to, bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertraline (Zoloft), sibutramine, trazodone (Dividose), and venlafaxine. Any other SSRI currently known or later developed are within the scope of the present disclosure.

In other embodiments, the second compound in the above pharmaceutical composition is a serotonin/norepinephrine reuptake inhibitor (SNRI). Examples of SNRIs include, but are not limited to, citalopram (Celexa), dulexetine, escitalopram (Lexapro), fluvoxamine (Luvox), and venfalaxine (effexor). Any other SNRI currently known or later developed are within the scope of the present disclosure.

In further embodiments, the second compound in the above pharmaceutical composition is a monoamine oxidase inhibitor (MAO-I). Examples of MAO-Is include, but are not limited to, tranylcypromine (Parnate), phenelzine (Nardil), maprotiline, and isocarboxazid (Marplan). Any other MAO-I currently known or later developed are within the scope of the present disclosure.

In yet other embodiments, the second compound in the above pharmaceutical composition is a tricyclic antidepressant (TCA). Examples of TCAs include, but are not limited to, amitryptiline (Norpramine), amoxapineclomipramine (Anafranil), desipramine, doxepin (Sinequan), imipramine (Tofranil), maprotiline, (Elavil), protryptiline, and trimipramine. Any other TCA currently known or later developed are within the scope of the present disclosure.

In some other embodiments, the second compound in the above pharmaceutical composition is a compound selected from aripiprazole (Abilify), clozapine, fluoxetine/olanzapine (Symbyax), olanzapine (Zyprexa), quetiapine (Seroquel), risperidone (Risperdal), valproic acid (Depakote), and ziprasidone (Geodon). Any other atypical antidepressant currently known or later developed are within the scope of the present disclosure.

In some embodiments, the second compound in the above pharmaceutical composition is a compound selected from chlorpromazine (Thorazine®), mesoridazine (Serentil®), prochlorperazine (Compazine®), thioridazine (Mellaril®), haloperidol (Haldol®), pimozide (Orap®), clozapine (Clozaril®), loxapine (Loxitane®), olanzapine (Zyprexa®), quetiapine (Seroquel®), resperidone (Resperidal®), ziprasidone (Geodon®), lithium carbonate, Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa.

In some embodiments, the second compound in the above pharmaceutical composition is an antipsychotic agent. The antipsychotic agent may be selected from the group consisting of a phenothiazine, phenylbutylpiperadine, debenzapine, benzisoxidil, and salt of lithium. The phenothiazine group of compounds may be selected from the group consisting of chlorpromazine (Thorazine®), mesoridazine (Serentil®), prochlorperazine (Compazine®), and thioridazine (Mellaril®). The phenylbutylpiperadine group of compounds may be selected from the group consisting of haloperidol (Haldol®), and pimozide (Orap®). The debenzapine group of compounds may be selected from the group consisting of clozapine (Clozaril®), loxapine (Loxitane®), olanzapine (Zyprexa®) and quetiapine (Seroquel®). The benzisoxidil group of compounds may be selected from the group consisting of resperidone (Resperidal®) and ziprasidone (Geodon®). The salt of lithium may be lithium carbonate. In some embodiments, the antipsychotic agent may be selected from the group consisting of Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa, or pharmaceutically acceptable salts thereof.

In other embodiments, the second compound in the above pharmaceutical composition is a norepinephrine reuptake inhibitor. The norepinephrine reuptake inhibitor is selected from the group consisting of thionisoxetine and reboxetine.

In further embodiments, the second compound in the above pharmaceutical composition is a dopamine agonist. The dopamine agonist may be selected from the group consisting of sumatriptan, almotriptan, naratriptan, frovatriptan, rizatriptan, zomitriptan, cabergoline, amantadine, lisuride, pergolide, ropinirole, pramipexole, and bromocriptine.

In yet another embodiment, the second compound in the above pharmaceutical composition is an anti-insomnia drug. Examples of anti-insomnia drugs include, but are not limited to, alprazolam (Xanax), chlordiazepoxide (Librium, Limbitrol), clorazepate (Tranxene), estazolan (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. Any other anti-insomnia drug currently known or later developed are within the scope of the present disclosure.

In other embodiments, the second compound in the above pharmaceutical composition is an anti-manic drug. Examples of anti-manic drugs include, but are not limited to, divalproex (Depakote), lithium carbonate (Eskalith), and lithium citrate. Any other anti-manic drug currently known or later developed are within the scope of the present disclosure.

In some embodiments, the second compound in the above pharmaceutical composition is an anti-phobia drug. An example of anti-phobia drugs includes, but is not limited to, D-cycloserine. Those of skill in the art recognize that some of the other drugs disclosed herein also work as anti-phobia drugs. Any other anti-manic drug currently known or later developed are within the scope of the present disclosure.

In another embodiment, the first or second compound in the above pharmaceutical composition is a serotonin 2A antagonist. The serotonin 2A antagonist may be M 100,907 or an analog thereof. By "M 100,907," it is meant the compound of Formula II.

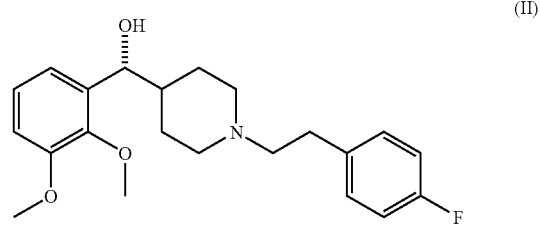

(II)

In some embodiments, the first compound of the pharmaceutical composition is Formula (I) and the second compound of the composition is Formula (II). In other embodiments, the first compound of the pharmaceutical composition is Formula (II) and the second compound of the composition is selected from the group consisting of a SSRI including but not limited to bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine; a SNRI including but not limited to citalopram (Celexa), dulexetine, escitalopram (Lexapro), fluvoxamine (Luvox), and venfalaxine (effexor); a MAO-I including but are not limited to tranylcypromine (Parnate), phenelzine (Nardil), maprotiline, and isocarboxazid (Marplan); a TCA including but not limited to amitryptiline (Norpramine), amoxapineclomipramine (Anafranil), desipramine, doxepin (Sinequan), imipramine (Tofranil), maprotiline, (Elavil), protryptiline, and trimipramine; aripiprazole (Abilify); clozapine; fluoxetine/olanzapine (Symbyax); olanzapine (Zyprexa); quetiapine (Seroquel); risperidone (Risperdal); valproic acid (Depakote); ziprasidone (Geodon); chlorpromazine (Thorazine®); mesoridazine (Serentil®); prochlorperazine (Compazine®); thioridazine (Mellaril®); haloperidol (Haldol®); pimozide (Orap®); clozapine (Clozaril®); loxapine (Loxitane®); olanzapine (Zyprexa®); quetiapine (Seroquel®); resperidone (Resperidal®); ziprasidone (Geodon®); lithium carbonate; Aripiprazole (Abilify); Clozapine; Clozaril; Compazine; Etrafon; Geodon; Haldol; Inapsine; Loxitane; Mellaril; Moban; Navane; Olanzapine (Zyprexa); Orap; Permitil; Prolixin; Phenergan; Quetiapine (Seroquel); Reglan; Risperdal; Serentil; Seroquel; Stelazine; Taractan; Thorazine; Triavil; Trilafon; Zyprexa; an antipsychotic agent including but not limited to a phenothiazine such as chlorpromazine (Thorazine®), mesoridazine (Serentil®), prochlorperazine (Compazine®), and thioridazine (Mellaril®), a phenylbutylpiperadine such as haloperidol (Haldol®) and pimozide (Orap®), a debenzapine such as clozapine (Clozaril®), loxapine (Loxitane®), olanzapine (Zyprexa®) and quetiapine (Seroquel®), a benzisoxidil such as resperidone (Resperidal®) and ziprasidone (Geodon®), a salt of lithium such as lithium carbonate, Aripiprazole (Abilify), Etrafon Haldol, Inapsine, Mellaril, Moban, Navane, Permitil, Prolixin, Phenergan, Reglan, Risperdal, Stelazine, Taractan, Triavil, and Trilafon; a norepinephrine reuptake inhibitor including but not limited to thionisoxetine and reboxetine; a dopamine agonist including but not limited to sumatriptan, almotriptan, naratriptan, frovatriptan, rizatriptan, zomitriptan, cabergoline, amantadine, lisuride, pergolide, ropinirole, pramipexole, and bromocriptine; an anti-insomnia drug including but not limited to alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs; an anti-manic drug including but not limited to divalproex (Depakote), lithium carbonate (Eskalith), and lithium citrate; an anti-phobia drug including but not limited to D-cycloserine; and pharmaceutically acceptable salts thereof.

In some embodiments, the pharmaceutical compositions described herein are used to treat disorders disclosed in U.S. patent application Ser. No. 10/759,561, filed on Jan. 15, 2004, by Weiner et al., and entitled "SELECTIVE SEROTONIN 2A/2C RECEPTOR INVERSE AGONISTS AS THERAPEUTICS FOR NEURODEGENERATIVE DISEASES," which is hereby incorporated by reference herein in its entirety, including any drawings.

It is understood by those of skill in the art that the compounds disclosed herein may be present as the compounds themselves, or as pharmaceutically acceptable salts, esters, amides, or prodrugs thereof, all of which are contemplated by the present invention.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R+, where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on any of the compounds disclosed herein can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In some embodiments, the pharmaceutical composition described herein further comprises a physiologically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

What is claimed is:

1. A pharmaceutical composition comprising:
a first compound of Formula (I)

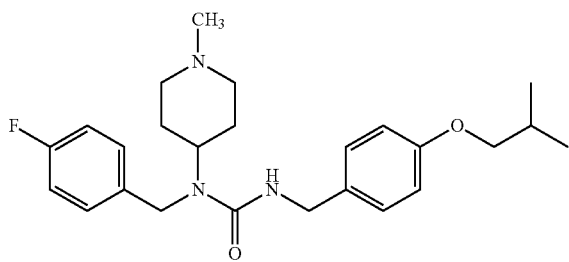

or a pharmaceutically acceptable salt thereof, and a MAO-I or a pharmaceutically acceptable salt thereof.

2. The pharmaceutical composition of claim 1 wherein the MAO-I is selected from the group consisting of tranylcypromine (Parnate), phenelzine (Nardil), maprotiline, and isocarboxazid (Marplan).

3. The pharmaceutical composition of claim 1, further comprising a physiologically acceptable carrier, diluent, or excipient, or a combination thereof.

4. The composition of claim 1, wherein the compound of formula (I) is the free base.

5. The composition of claim 1, wherein the composition is in a single unit dosage form.

6. The composition of claim 5, wherein the composition is in a single unit dosage fowl suitable for oral administration to a human.

7. The composition of claim 6, wherein the dosage form is solid.

8. The composition of claim 7, wherein the composition is in the form of a tablet or a capsule.

9. The composition of claim 8, wherein the composition is in the form of a tablet.

10. The composition of claim 1, wherein the amount of the compound of formula (I), or a pharmaceutically acceptable salt thereof, is from about 0.1 mg to about 500 mg.

11. The composition of claim 1, wherein the amount of the compound of formula (I), or a pharmaceutically acceptable salt thereof, is from about 1 mg to about 40 mg.

* * * * *

UNITED STATES PATENT AND TRADEMARK OFFICE
CERTIFICATE OF CORRECTION

| | | |
|---|---|---|
| PATENT NO. | : 7,875,632 B2 | Page 1 of 1 |
| APPLICATION NO. | : 12/378385 | |
| DATED | : January 25, 2011 | |
| INVENTOR(S) | : Weiner et al. | |

It is certified that error appears in the above-identified patent and that said Letters Patent is hereby corrected as shown below:

Claim 6, column 28, line 6, the word "fowl" should be replaced with --form--.

Signed and Sealed this
Nineteenth Day of April, 2011

David J. Kappos
*Director of the United States Patent and Trademark Office*